US011441012B2

(12) United States Patent
Laurichesse et al.

(10) Patent No.: US 11,441,012 B2
(45) Date of Patent: Sep. 13, 2022

(54) USE OF AT LEAST ONE PHENOLIC COMPOUND TO STABILISE ETHYLENE COPOLYMERISATION REACTIONS

(71) Applicant: SK GLOBAL CHEMICAL CO., LTD., Seoul (KR)

(72) Inventors: Christian Laurichesse, Lons (FR); Thibaut Severac, Villeurbanne (FR); Angélique Lelievre, Bambiderstroff (FR); Claire Isabelle Michalowicz, Evreux (FR); Louis Defoor, Lons (FR); Yves Cabon, Metz (FR)

(73) Assignee: SK GLOBAL CHEMICAL CO., LTD., Seoul (KR)

( * ) Notice: Subject to any disclaimer, the term of this patent is extended or adjusted under 35 U.S.C. 154(b) by 60 days.

(21) Appl. No.: 16/468,033

(22) PCT Filed: Dec. 22, 2017

(86) PCT No.: PCT/FR2017/053823
§ 371 (c)(1),
(2) Date: Jun. 10, 2019

(87) PCT Pub. No.: WO2018/115790
PCT Pub. Date: Jun. 28, 2018

(65) Prior Publication Data
US 2020/0010640 A1     Jan. 9, 2020

(30) Foreign Application Priority Data
Dec. 23, 2016   (FR) ...................... 1663341

(51) Int. Cl.
C08K 5/1545 (2006.01)
C07D 311/72 (2006.01)
C08F 210/02 (2006.01)
C08L 23/06 (2006.01)
C08L 23/08 (2006.01)

(52) U.S. Cl.
CPC .......... C08K 5/1545 (2013.01); C07D 311/72 (2013.01); C08F 210/02 (2013.01); C08L 23/06 (2013.01); C08L 23/08 (2013.01)

(58) Field of Classification Search
CPC .......... C08L 23/06; C08L 23/08; C08K 5/13; C08K 5/1545; C07D 311/72; C08F 210/02; C08F 2410/01
See application file for complete search history.

(56) References Cited

U.S. PATENT DOCUMENTS

| | | | |
|---|---|---|---|
| 2006/0141275 A1* | 6/2006 | Yamashita | B32B 27/36 428/480 |
| 2006/0149004 A1 | 7/2006 | Lee et al. | |
| 2007/0032614 A1 | 2/2007 | Goossens et al. | |
| 2011/0184129 A1 | 7/2011 | Mähling et al. | |
| 2012/0322956 A1* | 12/2012 | Schmidt | C08F 110/02 526/60 |
| 2015/0073104 A1* | 3/2015 | Uematsu | C08F 110/02 526/64 |

FOREIGN PATENT DOCUMENTS

| | | |
|---|---|---|
| DE | 2946954 A1 | 6/1981 |
| DE | 102009023651 A1 | 12/2010 |
| WO | 2007135031 A1 | 11/2007 |
| WO | 2013149698 A1 | 10/2013 |

OTHER PUBLICATIONS

Kajiyama, T. et al.; Polymer Degradation and Stability, 2001, vol. 71, p. 445-452.*
ISA/EP; International Search Report and Written Opinion for International Application No. PCT/FR2017/053823 dated Mar. 5, 2018, 12 pages.
Y.C. Ho et al. "Vitamin E based stabilizer components in HDPE polymer", Journal of Vinyl and Additive Technology, vol. 4, No. 2, Jun. 1, 1998, pp. 139-150.
Toyoda, J. et al. "Push-pull modulation of ganglion cell responses of carp retina by amacrine cells," Neuroscience Letters, Elsevier, Amsterdam, NL, vol. 142, No. 1, Aug. 3, 1992, pp. 41-44.

* cited by examiner

Primary Examiner — Robert S Jones, Jr.
(74) Attorney, Agent, or Firm — Buchanan Ingersoll & Rooney P.C.

(57) ABSTRACT

A method of stabilizing radical ethylene copolymerization reactions for approximately 5 to 10 minutes, the method including using a phenolic compound with other comonomers and performing the radical ethylene copolymerization reactions at high pressure. Also, a method of preparing an ethylene copolymer at high pressure in the presence of one or more phenolic compounds, as defined below, and one or more initiators.

16 Claims, No Drawings

USE OF AT LEAST ONE PHENOLIC COMPOUND TO STABILISE ETHYLENE COPOLYMERISATION REACTIONS

CROSS-REFERENCE TO RELATED APPLICATION

This application is a U.S. National Stage application of International Application No. PCT/FR2017/053823, filed on 22 Dec. 2017, which claims the benefit of French Patent Application No. 1663341, filed 23 Dec. 2016.

The present invention relates to the use of one or more phenolic compounds, as defined below, to stabilise ethylene copolymer reactions at high pressure.

The invention also relates to a method of preparing an ethylene copolymer at high pressure in the presence of one or more phenolic compounds, as defined below, and one or more initiators.

Low-density polyethylenes (also known as LDPE) and ethylene copolymers are usually prepared in an autoclave or tubular reactor under very high pressure, by continuous introduction of ethylene, of one or more optional comonomers and of one or more initiators, such as organic peroxides, typically diluted in an organic solvent. The pressure inside the reactor is typically comprised from 500 to 5000 bar while the temperature, during reaction initiation, most often varies from 80 to 250° C. The maximum reaction temperature is typically comprised from 120 to 350° C.

The degree of conversion into polymer generally obtained with this type of method is on the order of from 15% to 25%. Similarly, the productivity of a method, expressed in grams of polyethylene or ethylene copolymer produced per gram of peroxide initiator used, may vary from 1000 to 3000 g/g, and is often less than 2500 g/g.

Producers of polyethylene and ethylene copolymer are constantly seeking to obtain production gains and thus streamline costs. In particular, it is important to seek to implement a method enabling the manufacture of polyethylene or ethylene copolymers at a high rate of productivity while maintaining good reliability.

This increased productivity gain is all the more important as polyethylenes and ethylene copolymers are of particular commercial interest because they can be used in various fields of application due to their compatibility with many other polymers or resins.

For example, ethylene copolymers can be used to manufacture cables, thermomelt adhesive compositions, multi-layer wrapping films, or masterbatches. They can also be used as impact modifiers in the preparation of polymers such as polyamides and polyesters for the electronics and automotive sectors.

However, producers of polyethylene and ethylene copolymer frequently encounter phenomena such as runaway reactions and thermal decomposition of the ethylene because such reactions are performed at high temperature and high pressure.

In particular, under these operating conditions, during the polymerisation reaction in the presence of excess initiators (organic peroxides, oxygen), ethylene decomposes explosively by leading to the formation of carbon, methane and hydrogen.

These parasite reactions in the degradation of the ethylene due to excessive initiators, under the aforementioned operating conditions, lead at best to the production of coloured granules (soft decomposition), and at the worst to a rapid rise in pressure and temperature (violent decomposition) in the reactor that triggers production stoppage and costly maintenance operations.

Thus, one of the purposes of the present invention is to reduce the frequency of the ethylene decomposition during ethylene copolymerisation processes at high pressure in order to improve their productivity and reduce the maintenance costs associated with this decomposition.

In other words, there is a real need to implement a method for copolymerising ethylene wherein the ethylene copolymer reactions at high pressure are stabilised by minimising the risk of ethylene degradation.

The document WO 2013/149698 describes the use of hindered phenolic compounds to reduce fouling in the polyethylene polymerisation reactors.

In particular, this document discloses that a mixture consisting of ethylene and one or more optional comonomers is heated to a temperature that is sufficient to allow organic peroxides, when introduced into the mixture, to decompose into free radicals in order to more effectively trigger polymerisation. Thus, the monomer mixture is preheated prior to the introduction of the organic peroxides, at the start of the reactor in equipment provided for this purpose.

However, during this preheating step, this reaction mixture tends to polymerise easily on the preheater walls.

This unwanted polymerisation results in limiting the heat transfer to the organic peroxides, which prevents them from forming free radicals and enabling polymerisation to start under optimal operating conditions. This parasite reaction fouls the walls of the device used for preheating.

The hindered phenolic compounds are thus added to the monomer mixture prior to the introduction of organic peroxides in order to reduce or eliminate parasite polymerisation occurring during the preheating stage and therefore reduce fouling at the beginning of the reactor. In other words, the phenolic compounds are used to reduce the parasite polymerisation that occurs in the monomer mixture before the radical polymerisation initiated by organic peroxides begins in the reaction area.

This document therefore does not describe the use of phenolic compounds to decrease the frequency of ethylene decomposition during high pressure polymerisation, i.e. in the presence of organic peroxides acting as polymerisation initiators.

Therefore, one particular subject-matter of the invention is the use of at least one phenolic compound of the following Formula (I):

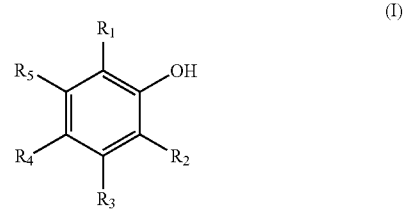

Formula (I), wherein:
$R^1$ represents:
a hydrogen atom;
a linear $C_1$-$C_8$ alkyl radical;
a linear $C_1$-$C_8$ hydroxyalkyl radical;
a hydroxy group;

$R^2$, $R^3$, $R^4$ and $R^5$, identical or different, represent:
a hydrogen atom;
a $C_1$-$C_8$ alkyl radical, linear or branched, optionally substituted by one or more hydroxy radicals;
a $C_1$-$C_8$ alkoxy radical, linear or branched, optionally substituted by one or more hydroxy radicals;
a hydroxy group,
it being understood that $R^4$ and $R^5$ can together form a five- or six-member cycle comprising an oxygen atom; said cycle being substituted by a $C_1$-$C_{17}$ alkyl radical, linear or branched, in order to stabilise the radical ethylene copolymerisation reactions at high pressure in the presence of one or more initiators.

The phenolic compound(s) of Formula (I) present the advantage to significantly decrease the frequency of the ethylene decomposition in a reaction mixture comprising other monomers during the radical copolymerisation of the ethylene at high pressure in the presence of initiators.

In other words, the phenolic compound(s) according to the invention permit(s) to decrease the sensitivity of the ethylene to the concentration of the initiators (such as organic peroxides, oxygen) thereby limiting their degradation into carbon, methane, and hydrogen.

More generally, the phenolic compound(s) according to the invention permit(s) to improve the productivity of the ethylene copolymer preparation methods while minimising maintenance costs.

In particular, the phenolic compound(s) according to the invention has (have) the advantage of significantly reducing the frequency of the ethylene decomposition compared to the use of butyl hydroxytoluene under the same conditions.

The invention also relates to a method for preparing ethylene copolymers comprising a radical ethylene copolymerisation step at high pressure in the presence of one or more initiators and one or more phenolic compounds as defined above.

The method of preparation according to the invention offers a high level of productivity and reliability.

Indeed, the parasite ethylene degradation reactions, which hinder productivity in a conventional preparation method, are reduced.

The present invention also relates to a polymer composition obtained by radical copolymerisation of the ethylene at high pressure in the presence of one or more initiators and one or more phenolic compounds of Formula (I).

Within the meaning of the present invention, "high pressure" means a pressure greater than 50 MPa. Preferably, the pressure varies from 500 bar (50 MPa) to 3000 bar (300 MPa), preferably from 1200 bar (120 MPa) to 3000 bar (300 MPa), and more preferably from 1200 bar (120 MPa) to 2600 bar (260 MPa).

Other characteristics and advantages of the invention will be seen more clearly in the following description and examples.

In the following, and unless otherwise indicated, the ranges of values used in this document are inclusive.

The expression "at least one" is equivalent to the expression "one or more".

Phenolic Compound

Within the meaning of the invention, a "phenolic compound" is a compound comprising at least one phenol in its structure.

The phenolic compound(s) used to stabilise the reactions during the radical copolymerisation of the ethylene at high pressure are of Formula (I) as previously described.

According to Formula (I), $R^1$ does not represent a branched $C_1$-$C_8$ alkyl radical.

According to Formula (I), $R^4$ and $R^5$ can together form a five- or six-member cycle comprising an oxygen atom; said cycle being substituted by a $C_1$-$C_{17}$ alkyl radical, linear or branched.

Thus the phenol cycle can be condensed on a five- or six-member cycle comprising an oxygen atom; said cycle being substituted by a $C_1$-$C_{17}$ alkyl radical, linear or branched, preferably branched.

Preferably, the phenolic compound(s) correspond to the following Formula (I):

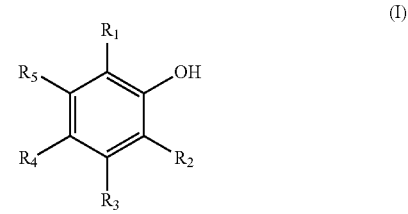

Formula (I), wherein:
$R^1$ represents:
a hydrogen atom;
a linear $C_1$-$C_4$ radical alkyl;
$R^2$, $R^3$ and $R^4$, identical or different, represent:
a hydrogen atom;
a $C_1$-$C_5$ radical alkyl, linear or branched;
a hydroxy group;
$R^5$ represents:
a hydrogen atom;
a $C_1$-$C_5$ radical alkyl, linear or branched;
a $C_1$-$C_5$ radical alkoxy, linear or branched;
a hydroxy group;
it being understood that $R^4$ and $R^5$ can together form a six-member cycle comprising an oxygen atom; said cycle being substituted by a branched $C_1$-$C_{17}$ alkyl radical.

Preferably, in Formula (I):
$R^1$, $R^2$ and $R^3$, identical or different, represent:
a hydrogen atom;
a linear $C_1$-$C_4$ alkyl radical; and
$R^4$ and $R^5$ together form a six-member cycle comprising an oxygen atom; said cycle being substituted by a branched $C_1$-$C_{17}$ alkyl radical.

More preferably, in Formula (I):
$R^1$, $R^2$ and $R^3$, identical or different, represent:
a hydrogen atom;
a methyl radical; and
$R^4$ and $R^5$ together form a six-member cycle comprising an oxygen atom; said cycle being substituted by a branched $C_1$-$C_{17}$ alkyl radical.

According to these embodiments, $R^1$, $R^2$ and $R^3$ can preferably represent a linear $C_1$-$C_4$, alkyl radical, in particular a methyl radical.

According to these embodiments, $R^1$ and $R^3$ can preferably represent a linear $C_1$-$C_4$ alkyl radical, in particular a methyl radical, and $R^2$ represents a hydrogen atom.

According to these embodiments, $R^2$ and $R^3$ can preferably represent a linear $C_1$-$C_4$ alkyl radical, in particular a methyl radical, and $R^1$ represents a hydrogen atom.

According to these embodiments, $R^1$ and $R^2$ can preferably represent a hydrogen atom and $R^3$ represents a linear $C_1$-$C_4$ alkyl radical, in particular a methyl radical.

In other words, the phenolic compound(s) is or are preferentially chosen from the following Formula (I'):

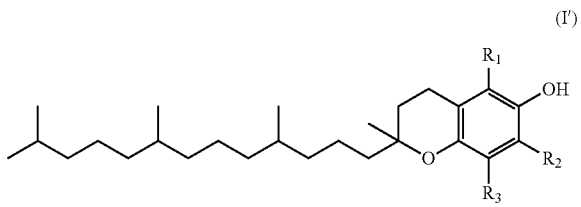

(I')

Formula (I') wherein $R^1$, $R^2$ and $R^3$ correspond to the previously-described meanings, in particular those mentioned above in the preferred embodiments.

Preferably, as an alternative, in Formula (I):
$R^1$, $R^2$, $R^3$ and $R^5$ represent a hydrogen atom; and
$R^4$ represents a $C_1$-$C_5$ alkoxy radical, preferably a methoxy radical.

Also preferably, as a variant, in Formula (I):
$R^1$ and $R^3$ represent a hydrogen atom;
$R^2$ and $R^5$ represent a branched $C_1$-$C_8$ alkyl radical, preferably a branched $C_1$-$C_5$ alkyl radical, in particular $C_4$;
$R^4$ represents a hydroxy group.

Preferably, the phenolic compound of Formula (I) is chosen from 2,5-di-tert-butylhydroquinone, 2,5-di(tert-amyl)hydroquinone, vitamin E and monomethyl ether hydroquinone (MEHQ) and mixtures thereof.

More preferably, the phenolic compound(s) according to the invention is or are chosen from vitamin E and monomethyl ether hydroquinone (MEHQ).

Even more preferably, the phenolic compound according to the invention is vitamin E.

In other words, the phenolic compound according to the invention corresponds to Formula (I').

Use

The phenolic compound(s) of Formula (I) is or are used to stabilise the radical ethylene copolymerisation reactions at high pressure in the presence of one or more initiators.

In other words, the phenolic compound(s) of Formula (I) are used to stabilise the radical ethylene copolymerisation reactions at high pressure initiated by one or more initiators.

In still other terms, the phenolic compound(s) of Formula (I) is or are used in a reaction mixture comprising at least ethylene and one or more initiators to stabilise the radical ethylene copolymerisation reactions at high pressure.

Within the meaning of this invention, "stabilise the radical ethylene copolymerisation reactions" means reducing the reactions of the decompostion (or degradation) of the ethylene into carbon, hydrogen and methane that occur during the radical copolymerisation reaction of the ethylene and are caused by excess initiators (organic peroxides and/or oxygen).

In other words, the phenolic compound(s) of Formula (I) is or are used to limit the decomposition of the ethylene during radical ethylene copolymerisation reactions at high pressure.

More specifically, the phenolic compound(s) is or are used to limit the number and speed of the reactions of the ethylene decomposition into carbon, hydrogen and methane during radical ethylene copolymerisation reactions at high pressure that are initiated by one or more initiators.

The initiator(s) enable(s) free radicals to be formed in order to initiate the radical copolymerisation of the ethylene.

In other words, the initiator(s) can trigger the radical copolymerisation of the ethylene.

The initiator(s) can be chosen from the organic peroxides, oxygen, azobisisobutyronitrile (AIBN) and mixtures thereof.

Preferably, the initiator(s) is or are chosen from the organic peroxides, oxygen and mixtures thereof.

Yet more preferably, the initiator(s) is or are chosen from the organic peroxides.

Preferably, the organic peroxides are chosen from the peroxy esters, dialkyl peroxides, hydroperoxides or peroxyketals.

Such peroxides are in particular marketed by Arkema under the brand name Luperox®.

Examples of peroxy esters can include t-butyl peroxy-2-ethylhexanoate (Luperox 26), t-butyl peroxyacetate (Luperox 7), t-amyl peroxyacetate (Luperox 555), t-butyl perbenzoate (Luperox P), t-amyl perbenzoate (Luperox TAP) and OO-t-butyl 1-(2-ethylhexyl)monoperoxycarbonate (Luperox TBEC).

Examples of dialkyl peroxides can include 2,5-dimethyl-2,5-di-(t-butylperoxy)hexane (Luperox 101), dicumyl peroxide (Luperox DC), 1'alpha-alpha'-bis (t-butylperoxy) diisopropylbenzene (Luperox F40), di-t-butyl-peroxide (Luperox DI), di-t-amyl-peroxide (Luperox DTA) and 2,5-dimethyl-2,5-di-(t-butylperoxy)hexyne-3 (Luperox 130).

For hydroperoxide, tert-butyl-hydroperoxide (Luperox TBH 70) can be mentioned.

Examples of peroxyketals can include 1,1-di-(t-butylperoxy)-3,3,5-trimethylcyclohexane (Luperox 231), ethyl-3,3-di-(t-butylperoxybutyrate) (Luperox 233) or ethyl-3,3-di-(t-amylperoxybutyrate) (Luperox 533).

Preferentially, the organic peroxides are chosen from the dialkyl peroxides, particularly 2,5-dimethyl-2,5-di-(t-butylperoxy)hexane sold under the brand name Luperox 101.

The organic peroxide(s) is or are generally diluted in a solvent or a mixture of solvents. The solvent(s) can be chosen from the $C_1$-$C_{20}$ alkanes, particularly $C_3$-$C_{10}$, and more particularly $C_5$-$C_8$, and preferentially heptane.

The phenolic component(s) of Formula (I) are used in particular to stabilise the radical ethylene copolymerisation reactions with other comonomers.

Preferably, said comonomers are chosen from the unsaturated carboxylic acids (or their salts), the anhydrides of carboxylic acids, the vinyl esters such as vinyl acetate or pivalate acetate, the alpha-olefins such as propene, 1-butene, 1-hexene, 1-octene and 4-methyl-1-pentene, the unsaturated carboxylic acids such as (meth)acrylic acid, maleic acid and fumaric acid, the (meth)acrylic acid derivatives such as (meth)acrylonitrile and (meth)acrylic amide, the vinyl esters such as vinyl methyl ether and vinyl phenyl ether and the aromatic vinyl compounds such as styrene and alpha-methyl styrene, or carbon monoxide, or mixtures thereof.

More preferably, the comonomer(s) are chosen from esters of unsaturated carboxylic acids (or their salts), carboxylic acid anhydrides, and mixtures thereof.

The esters of unsaturated carboxylic acid are preferably chosen from the (meth)alkyl acrylates, particularly the $C_1$-$C_{24}$ (meth)alkyl acrylates, and the (meth)acrylates comprising an epoxy group.

Preferably, the alkyl (meth)acrylates are chosen from among methyl acrylate, ethyl acrylate, n-butyl acrylate, isobutyl acrylate, ethyl-2-hexyl acrylate, cyclohexyl acrylate, n-octyl acrylate, methyl methacrylate, ethyl methacrylate and butyl methacrylate.

Preferably, the (meth)acrylates comprising an epoxy group are chosen from among glycidyl methacrylate, glycidyl acrylate.

Preferably, the phenolic compound(s) of Formula (I) are used to stabilise the radical ethylene copolymerisation reactions with comonomers chosen from a mixture of unsaturated carboxylic acid esters and the anhydrides of carboxylic acid in the presence of one or more initiators.

Even more preferably, the phenolic compound(s) of Formula (I) is or are used to stabilise the ethylene copolymerisation reactions with a mixture of comonomers comprising methyl acrylate and glycidyl methacrylate.

Even more preferably, the phenolic compound(s) of Formula (I) are used to stabilise the radical ethylene copolymerisation reactions between the ethylene and a mixture of comonomers comprising methyl acrylate and glycidyl methacrylate in the presence of one or more initiators chosen from the organic peroxides, oxygen, or mixtures thereof.

Method

As previously explained, the invention also relates to a method for preparing ethylene copolymers that includes a radical ethylene copolymerisation step at high pressure in the presence of one or more initiators as described above, and one or more phenolic compounds as described above.

Preferably, the initiator(s) is or are chosen from the organic peroxides, oxygen, and mixtures thereof.

Preferably, the phenolic compound(s) according to the invention is or are chosen from vitamin E and monomethyl ether hydroquinone (MEHQ).

Even more preferably, the phenolic compound according to the invention is vitamin E. In other words, the phenolic compound corresponds to the previous Formula (I').

The phenolic compound(s) is or are preferably present in an amount by weight comprised from 100 to 50,000 ppm relative to the amount by weight of the comonomers.

Preferably, the phenolic compound(s) is or are solubilised in an organic solvent, preferably a hydrocarbon-, alcohol-, or ketone-type organic solvent, yet more preferably a hydrocarbon-type organic solvent, in particular isododecane, before being introduced into the reactor, preferably in an amount of from 5 and 80% by weight, relative to the amount by weight of the solvent.

Alternatively, the phenolic compound(s) is or are solubilised in the comonomer(s) before being introduced into the reactor, preferably in an amount by weight of 100 to 50,000 ppm relative to the amount by weight of the comonomer(s).

The initiator(s) is or are preferably present in an amount by weight of between 20 and 1000 ppm relative to the amount by weight of the ethylene.

The copolymerisation of the ethylene is done at an initiation temperature of from 100 to 200° C., preferably from 120 to 160° C.

The copolymerisation takes place at a pressure of from 500 bar (50 MPa) to 3000 bar (300 MPa), preferably from 1200 bar (120 MPa) to 3000 bar (300 MPa), more preferably from 1200 bar (120 MPa) to 2600 bar (260 MPa).

The high pressure copolymerisation is generally carried out in an autoclave or tubular reactor. The reaction temperature is generally comprised from 150 to 320° C.

When a tubular reactor is used, the mixture of ethylene and any comonomer(s) is preferably introduced at the top of the tubular reactor. The initiator or mixture of initiators is injected with a high-pressure pump at the top of the reactor, downstream of the inlet for the mixture of ethylene and any comonomer(s).

The mixture of the ethylene and any optional comonomers can be injected at at least one other point of the reactor; this injection is followed by a repeat injection of initiator or mixture of initiators, known as the multipoint injection technique. When the multipoint injection technique is used, the mixture is preferably injected such that the weight ratio of the mixture injected on input into the reactor to the total mixture injected is comprised from 10 to 90%.

Other methods of tubular high-pressure polymerisation or copolymerisation that can be used are for example those disclosed in US2006/0149004 A1 or in US2007/0032614 A1.

An autoclave reactor can also be used to carry out the high-pressure radical polymerisation. An autoclave reactor generally consists of a cylindrical reactor into which a stirrer is placed. The reactor can be separated into several zones connected to one another in sequence.

Preferably, the method according to the invention is implemented in an autoclave reactor.

Advantageously, the time spent in the reactor is comprised from 30 to 120 seconds.

Preferentially, the length/diameter ratio of the reactor is comprised from 3 to 25. The ethylene and comonomer(s) are injected into the reaction area(s) at a temperature comprised from 50 to 120° C.

Preferably, the ethylene and comonomer(s) are injected into the reaction area(s) at a temperature strictly below 100° C., preferably at a temperature strictly below 80° C.

Preferably, the method for preparing ethylene copolymers according to the invention does not include a preheating step of the monomers prior to their introduction into the reaction area(s).

Preferably, the injection of one or more initiators into the reaction mixture begins at a temperature strictly below 100° C., preferably at a temperature strictly below 80° C.

Preferably, the method for preparing ethylene copolymers according to the invention does not include a preheating step of the monomers prior to the introduction of said one or more initiators.

Alternatively, an initiator is also injected into this first reaction area when the reaction area reaches a temperature comprised from 150 to 200° C.

During the reaction the temperature can be comprised from 150 to 320° C. because the reaction is exothermic. If the reactor is a multizone reactor, the feed of ethylene and any optional comonomers which have not reacted as well as the polymer formed then go through the subsequent reaction zones.

In each reaction area, ethylene, comonomers and initiators can be injected at an initiation temperature comprised from 150 to 200° C. The temperature of the zones after initiation is comprised from 150 to 320° C.

The reactor pressure varies from 500 bar (50 MPa) to 3000 bar (300 MPa), preferably from 1200 bar (120 MPa) to 3000 bar (300 MPa), more preferably from 1200 bar (120 MPa) to 2600 bar (260 MPa).

Product Resulting from the Polymeriseable Composition

Another subject-matter of the present invention relates to the product resulting from the radical ethylene copolymerisation at high pressure in the presence of one or more initiators as described above and of one or more phenolic compounds as described above.

Thus the product is a polymer composition (or polymer product) that is a result of the radical ethylene copolymerisation at high pressure between the ethylene and other comonomers in the presence of one or more initiators as described above and of one or more phenolic compounds as described above.

The polymer product or polymer composition thus obtained can be used in any type of application, in particular for packaging, and notably food packaging.

Preferably, the initiator(s) is or are chosen from the organic peroxides, oxygen and mixtures thereof.

The polymer composition comprises the ethylene copolymer and the phenolic compound(s) as described above.

Preferably, the phenolic compound(s) is or are chosen from vitamin E and monomethyl ether hydroquinone (MEHQ).

Even more preferably, the polymer composition comprises vitamin E. In other words, the phenolic compound corresponds to the previous Formula (I').

Once the copolymer has been obtained, one or more additives can be added to the polymer composition.

The additive is preferably chosen from the antioxidants, UV protection agents, and processing agents, for the purposes of improving the final appearance when it is used, such as fatty amides, stearic acid and its salts, ethylenebisstearamide or fluoropolymers; antifogging agents; antiblocking agents such as silica or talc; fillers such as calcium carbonate and nanofillers such as, for example, clays; coupling agents such as silanes; crosslinking agents such as peroxides different to those used as radical copolymerisation initiators; antistatic agents; nucleating agents; pigments; dyes; plasticisers; fluidisers and flame-retardant additives such as aluminium hydroxide or magnesium hydroxide.

These additives are generally used at contents comprised from 10 ppm to 10,000 ppm by weight relative to the weight of the final polyethylene or ethylene copolymer.

The plasticisers, fluidisers and flame-retardant additives can be present in amounts well above 10,000 ppm.

The following examples serve to illustrate the invention, without, however, being limiting in nature.

EXAMPLES

The following examples were performed on a 110 ml continuous stirred autoclave micro-pilot.

This equipment operates continuously at pressures comprised from 500 to 2200 bar. The reactor wall temperature is set at 200° C. by means of heater rods placed in the walls of the reactor. Stirring is at 1540 rpm (revolutions per minute).

The temperature of the reaction medium in the reactor is measured by means of four thermocouples.

The reaction mixture is comprised of an ethylene mixture and acrylates which continuously flows into the reactor with residence time that can vary from 30 seconds to 120 seconds. The stabilising agent (phenolic compound) is introduced in mixture with acrylates.

The polymerisation initiator is continuously introduced into the reactor in amounts that enable a temperature of about 210° C. to be reached. When exiting the reactor, the polymer/monomer mixture is directly decompressed to three bars and the polymer is separated from the ethylene/acrylates mixture that did not react through a separation pot.

Operating Conditions:
Reactor flow: 4 kg/hr,
Peroxide used: Diluted Luperox 11 (tert-butyl peroxypivalate) in n-Heptane,
Residence time in the reactor: approx. 50 seconds,
Pressure: 1900 bar (190 Mpa),
Monomers: mixture of acrylates (methyl acrylate and glycidyle methacrylate with mass weights of respectively 5% and 1.5% in feed),
Stabilising agents: variable amounts that are introduced with acrylic monomers.

When the reaction has stabilised at the temperature of about 210° C. for approximately 5 to 10 min, the peroxide flow is then gradually increased every 4 minutes until decomposition is achieved (sometimes this limit is not reached), which enables the decomposition limits (or peroxide concentration sensitivity) to be determined.

The efficacy of the stabilising agent is determined by the amount of peroxides injected to achieve decomposition: the higher the amount of peroxide, the more effective the stabilising agent.

Trial #1: Testing with 230 ppm Moles of Stabilising Agent/Acrylate

In this trial, vitamin E was compared with butyl hydroxytoluene (BHT) with the same molar concentrations relative to acrylates. For each stabilising agent, a minimum of 3 trials was performed. The mean values for the trials are shown in the following table:

| Stabilising agents (phenolic compounds) | ppm mole stabilising agent relative to acrylates | Mean [C] Peroxide at decomposition in ppm moles |
|---|---|---|
| Without stabilising agent | — | 60.4 |
| BHT | 230 | 108.8 |
| Vitamin E | 230 | 120.0 |

The results show that Vitamin E enables greater stabilisation of the ethylene copolymerisation reactions, as ethylene decomposition is achieved at much higher concentrations of organic peroxides than with butyl hydroxytoluene (BHT).

In these trials, the mean values are significantly different.

Test #2: Testing with 460 ppm Moles of Stabilising Agent/Acrylate

In this trial, vitamin E and monomethyl ether hydroquinone (MEHQ) were compared with butyl hydroxytoluene (BHT) with the same molar concentrations relative to acrylates. For each stabilising agent, a minimum of 3 trials was performed. The mean values for the trials are shown in the following table:

| Stabilising agents (phenolic compounds) | ppm mole stabilising agent relative to acrylates | Mean [C] Peroxide at decomposition in ppm moles |
|---|---|---|
| Without stabilising agent | — | 60.4 |
| BHT | 460 | 92.9 |
| MEHQ | 460 | 97.3 |
| Vitamin E | 460 | 132.5 |

The results show that Vitamin E and monomethyl ether hydroquinone (MEHQ) enable greater stabilisation of the ethylene copolymerisation reactions than with butyl hydroxytoluene (BHT) as ethylene decomposition is achieved at much higher concentrations of organic peroxides.

Furthermore, the best results were obtained with Vitamin E.

In these trials, the mean values are significantly different.

Trials #3: Testing with 115 ppm Moles of Stabilising Agent/Acrylate

In this trial, vitamin E was compared with butyl hydroxytoluene (BHT) with the same molar concentrations relative to acrylates. For each stabilising agent, a minimum of 3 trials was performed. The mean values for the trials are shown in the following table:

| Stabilising agents (phenolic compounds) | ppm mole stabilising agent relative to acrylates | Mean [C] Peroxide at decomposition in ppm moles |
|---|---|---|
| Without stabilising agent | — | 60.4 |
| BHT | 115 | 77.2 |
| Vitamin E | 115 | 102.8 |

The results show that Vitamin E enables greater stabilisation of the ethylene copolymerisation reactions than with butyl hydroxytoluene (BHT) as ethylene decomposition is achieved at much higher concentrations of organic peroxides.

In these trials, the mean values are significantly different.

The invention claimed is:

1. A method of stabilizing radical ethylene copolymerization reactions for approximately 5 to 10 minutes, the method comprising using a phenolic compound with other comonomers, wherein the phenolic compound possesses a structure according to Formula (I):

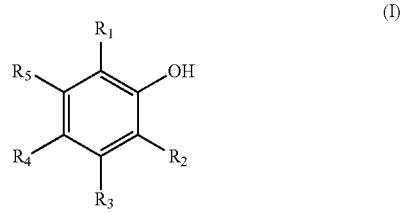

wherein:
  $R^1$ represents:
    a hydrogen atom;
    a linear $C_1$-$C_8$ alkyl radical;
    a linear $C_1$-$C_8$ hydroxyalkyl radical; or
    a hydroxy group;
  $R^2$, $R^3$, $R^4$ and $R^5$, identical or different, represent:
    a hydrogen atom;
    a $C_1$-$C_8$ alkyl radical, linear or branched, optionally substituted by one or more hydroxy radicals;
    a $C_1$-$C_8$ alkoxy radical, linear or branched, optionally substituted by one or more hydroxy radicals; or
    a hydroxy group, and
  it being understood that $R^4$ and $R^5$ can together form a five- or six-member cycle comprising an oxygen atom; said cycle being substituted by a $C_1$-$C_{17}$ alkyl radical, linear or branched;
  wherein the other comonomers comprise unsaturated carboxylic acid esters (or their salts), and optionally at least one other comonomer selected from the group consisting of carboxylic acid anhydrides, vinyl esters, alpha-olefins, unsaturated carboxylic acids, derivatives of (meth)acrylic acid, vinyl ethers, aromatic vinyl compounds, carbon monoxide, and mixtures thereof;
  wherein the unsaturated carboxylic acid esters include a $C_1$-$C_{24}$ (meth)alkyl acrylate and a (meth)acrylate possessing an epoxy group;
  wherein the method further comprises performing the radical ethylene copolymerization reactions at a high pressure in the presence of one or more initiators,
  wherein the method further includes a step of introducing a reaction mixture comprising ethylene and the comonomers into a reactor with a residence time of 30 to approximately 50 seconds and does not include a step in which the comonomers are preheated prior to the introduction of said one or more initiators, and
  wherein the method limits the decomposition of the ethylene during the radical ethylene copolymerization reactions at the high pressure.

2. The method of claim 1, wherein the radical copolymerization reactions are performed in an autoclave reactor.

3. The method of claim 2, further comprising injecting the one or more initiators into a reaction mixture at a temperature below 100° C.

4. The method of claim 1, wherein the radical copolymerization reactions are performed at a pressure from 50 MPa to 300 MPa.

5. A polymer composition obtained by radical ethylene copolymerization reactions according to claim 1.

6. The method of claim 1, wherein in Formula (I) of the phenolic compound:
  $R^1$ represents:
    a hydrogen atom; or
    a linear $C_1$-$C_4$ radical alkyl;
  $R^2$, $R^3$ and $R^4$, identical or different, represent:
    a hydrogen atom;
    a $C_1$-$C_5$ radical alkyl, linear or branched; or
    a hydroxy group;
  $R^5$ represents:
    a hydrogen atom;
    a $C_1$-$C_5$ radical alkyl, linear or branched;
    a $C_1$-$C_5$ radical alkoxy, linear or branched; or
    a hydroxy group; and
  it being understood that $R^4$ and $R^5$ can together form a six-member cycle comprising an oxygen atom; said cycle being substituted by a branched $C_1$-$C_{17}$ alkyl radical.

7. The method of claim 1, wherein in Formula (I) of the phenolic compound:
  $R^1$, $R^2$ and $R^3$, identical or different, represent:
    a hydrogen atom; or
    a methyl radical; and
  $R^4$ and $R^5$ together form a six-member cycle comprising an oxygen atom; said cycle being substituted by a branched $C_1$-$C_{17}$ alkyl radical.

8. The method of claim 1, wherein the phenolic compound is chosen from Formula (I'):

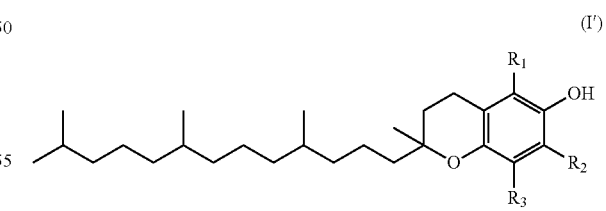

Formula (I'), wherein
  $R^1$, $R^2$ and $R^3$, identical or different, represent:
    a hydrogen atom; or
    a methyl radical.

9. The method of claim 1, wherein in Formula (I) of the phenolic compound:
  $R^1$, $R^2$, $R^3$ and $R^5$ represent a hydrogen atom; and
  $R^4$ represents a $C_1$-$C_5$ alkoxy radical.

10. The method of claim 1, wherein in Formula (I) of the phenolic compound:
$R^1$ and $R^3$ represent a hydrogen atom;
$R^2$ and $R^5$ represent a branched $C_3$-$C_8$ alkyl radical; and
$R^4$ represents a hydroxy group.

11. The method of claim 1, wherein the phenolic compound of Formula (I) is selected from the group consisting of 2,5-di-tert-butyl hydroquinone, 2,5-di(tert-amyl)hydroquinone, vitamin E and monomethyl ether hydroquinone.

12. The method of claim 1, wherein the phenolic compound of Formula (I) is vitamin E.

13. The method of claim 1, wherein the initiator(s) is or are selected from the group consisting of organic peroxides, oxygen azobisisobutyronitrile (AIBN) and mixtures thereof.

14. The method of claim 13, wherein the organic peroxides is or are selected from the group consisting of peroxy esters, dialkyl peroxides, hydroperoxides and peroxycetals.

15. The method according to claim 1, wherein the $C_1$-$C_{24}$ (meth)alkyl acrylate is selected from the group consisting of methyl acrylate, ethyl acrylate, n-butyl acrylate, isobutyl acrylate, ethyl-2-hexyl acrylate, cyclohexyl acrylate, n-octyl acrylate, methyl methacrylate, ethyl methacrylate and butyl methacrylate; and the (meth)acrylate possessing an epoxy group is selected from the group consisting of glycidyl methacrylate and glycidyl acrylate.

16. The method according to claim 15, wherein the $C_1$-$C_{24}$ (meth)alkyl acrylate is methyl acrylate, and the (meth)acrylate possessing an epoxy group is glycidyl methacrylate.

* * * * *